United States Patent [19]

Agrawal

[11] Patent Number: 5,296,364
[45] Date of Patent: Mar. 22, 1994

[54] MICROBIAL METHOD OF PRODUCING INOSITOL

[75] Inventor: Pramod Agrawal, Corpus Christi, Tex.

[73] Assignee: Cerechem Corporation, Carpinteria, Calif.

[21] Appl. No.: 904,372

[22] Filed: Jul. 21, 1992

[51] Int. Cl.$^5$ ............................................. C12P 7/02
[52] U.S. Cl. ................................... 435/155; 435/942
[58] Field of Search ............... 435/100, 105, 171, 155, 435/942

[56] References Cited

U.S. PATENT DOCUMENTS 2,615,053  10/1952  Artz et al. ............................ 568/833
5,064,762  11/1991  Robinowitz ........................... 435/942

FOREIGN PATENT DOCUMENTS 2-261387  10/1990  Japan ............................ C07C 35/16

OTHER PUBLICATIONS

White, Michael J., et al., "The OPI1 Gene of *Saccharomyces cerevisiae*, a Negative Regulator of Phospholipid Biosynthesis, (Encodes a Protein Containing Polyglutamine Tracts and a Leucine Zipper)," J. of Biol. Chem. 266: 863-872 (1991).

Greenberg, Miriam L., "Regulatory Mutations of Inositol Biosynthesis in Yeast: [Isolation of Inositol Excreting Mutants]," Genetics 100: 19-33 (1982).

Bailey, J., et al., "Biochemical Engineering Fundamentals," pp. 579-580, McGraw-Hill (1986).

Morris, E. O., Chapter VI, "Yeast Growth", pp. 275-285, 317-321, 1958.

Greenberg et al., "Characterization of a Yeast Regulatory Mutant Constitute for Synthesis of Inositol-1--Phosphate Syntheses", Mol. Gen. Genet. 186, 157-163, 1982.

*Primary Examiner*—Douglas W. Robinson
*Assistant Examiner*—Kristin Larson
*Attorney, Agent, or Firm*—David J. Larwood

[57] ABSTRACT

A method for increasing production of inositol from a nutrient medium is disclosed. The wild strain of *Saccharonyces cerrevisae* was modified by deleting the OPI1 gene locus. The modified strain was fermented in various media, both artificial and natural, to increase the production of inositol from the medium. Using a balanced synthetic nutrient medium, a glucose feed rate of 100 g/l and adding ammonium sulfate as a nitrogen source gave an almost 10-fold increase in inositol production, compared to production under more typical conditions. Using almond hull juice as a feedstock, batch conditions showed no measureable increase in inositol production but continuous fermentation yielded almost a 50% increase in inositol concentration.

11 Claims, 6 Drawing Sheets

MICROBIAL METHOD OF PRODUCING INOSITOL

FIELD OF THE INVENTION

Inositol has been commercially produced by extraction from numerous suitable plant juice extracts, notably corn steep liquor. Most plant juices contain considerable amounts of sugars and other growth nutrients. The present invention relates to a microorganism that will consume some quantity of undesired nutrients to produce greater quantities of inositol.

BACKGROUND OF THE INVENTION

Inositol is found in nature in a large number of plants. In yeast, and possibly higher animals, inositol appears to play an essential role in membrane phospholipid balance and is required for proper growth. Greenberg et al., *Genetics*, 100:19–33 (January 1982). The standard commercial source for inositol is corn steep liquor, since inositol is present as phytic acid in corn. See Artz et al., U.S. Pat. No. 2,615,053.

Greenberg et al. reported on regulatory mutations of inositol biosynthesis in yeast. They isolated several inositol excreting mutants of *Saccharomyces cerevisiae*. In this microorganism the enzyme inositol-1-phosphate synthase (I-1-P synthase), product of the INO1 gene locus, catalyzes the first step in inositol biosynthesis, i.e., the synthesis of inositol-1-phosphate from the substrate glucose-6-phosphate. In the wild type strain the activity of this enzyme is dramatically repressed in the presence of inositol. By selecting for mutants which overproduce and excrete inositol, Greenberg and coworkers idnetified mutants constitutive for inositol-1-phosphate synthase. Genetic analysis of the mutants indicated that at least three loci, designated OPI1, OPI2 and OPI4, direct inositol-mediated repression of I-1-P synthase. Mutants of these loci synthesize I-1-P synthase constitutively. Inositol excretion in the mutant strains was identified by replicating a colony of one of the excretory mutants onto selection plates followed by incubation for 5–10 days at 30° C. An inositol excreting mutant was identified as a phenotypically white colony surrounded by a red halo. The red halo signifies growth of the red indicator strain MC13 in the circular area into which the mutant is excreting inositol.

No quantitative measurement of the amount of inositol excretion by any of the mutants was made.

M. J. White, J. P. Hirsch and S. A. Henry have developed an inositol secreting strain of *S. cerevisiae* from which the OPI1 gene locus was removed. M. J. Hirsch, S. A. Henry, "The OPT 1 gene of *Saccharomyces cerevisiae*, a negative regulator of phospholipid biosynthesis, encodes a protein containing polyglutamine tracts and a leucine zipper," *J. Biol. Chem.*, 266, 863–872 (1991). For convenience, this strain is designated the YS2 strain. Removal of the OPI1 locus results in constitutively derepressed expression of inositol-1-phosphate synthase, the product of the INO1 gene. Many of the other enzymes involved in phospholipid biosynthesis are also expressed at high, derepressed levels. Therefore, the OPI1 gene is believed to encode a negative regulator that is required to repress a whole subset of structural genes encoding for phospholipid biosynthetic enzymes. Furthermore, the OPI1 gene was found to be non-essential to the organism since the YS2 strain so constructed is viable and exhibits a phenotype similar to that of previously isolated opi1 mutants. The YS2 strain accumulates INO1 mRNA constitutively to a level two- to three-fold higher than that observed in the wild-type cells. A sample, designated *S. cerevisiae*, YS2, was deposited on Feb. 13, 1991 with the American Type Culture Collection located at 12301 Parklawn Drive, Rockville, Md., Accession No. ATCC-74033.

M. J. White and S. A. Henry also developed an inositol-secreting strain of *S. cerevisiae* from which the OPI1 gene locus was removed and into which multiple copies of the INO1 gene were inserted. Southern blot analysis of the genomic DNA revealed the diploid strain to contain 6 or more copies of the INO1 gene. For convenience, this strain is designated the YS3 strain. A sample, designated *S. cerevisiae*, YS3, was deposited on Feb. 13, 1991 with the American Type Culture Collection in Rockville, Md., Accession No. ATCC-74034.

Adding the YS2 strain or the YS3 strain to a suitable nutrient medium and adjusting the nutrient medium according to the method of this invention allows significantly enhanced recovery of inositol.

SUMMARY OF INVENTION

The present invention describes a method of increasing the amount of inositol in a nutrient mixture using the OPI1 mutant of *S. cerevisiae* which was developed by M. White and S. Henry of Carnegie Mellon University (CMU) and which is the subject of a copending application, Ser. No. 07/640,495, filed Jan. 14, 1991, entitled "Inositol-Excreting Yeast."

The YS2 strain was deposited at ATCC on Feb. 13, 1991, strain designated *S. cerevisiae*, YS2, Accession No. ATCC-74033. as the feed stocks for the development of this method.

One object of the present invention is to provide a method of increasing the yield of inositol from a given volume of plant juice or other nutrient media.

Another object of this invention is to provide a method of producing inositol using the YS3 strain of *S. cerevisae* which contains multiple copies of the INO1 gene.

BRIEF DESCRIPTION OF THE DRAWINGS

The figures illustrate the concentration of various broth components over time under selected conditions.

DETAILED DESCRIPTION OF THE INVENTION

The general methods used are described in detail in the copending application entitled "Method of Purifying Cyclitols" by Pramod Agrawal and Israel Rabinowitz, Ser. No. 07/634,089, filed on Dec. 20, 1990, incorporated herein by reference. Those general methods include preparing a balanced synthetic nutrient medium, fermentation conditions, isolation of products and analytical methods. Those general methods were modified as described below with the following results.

Figure 1:
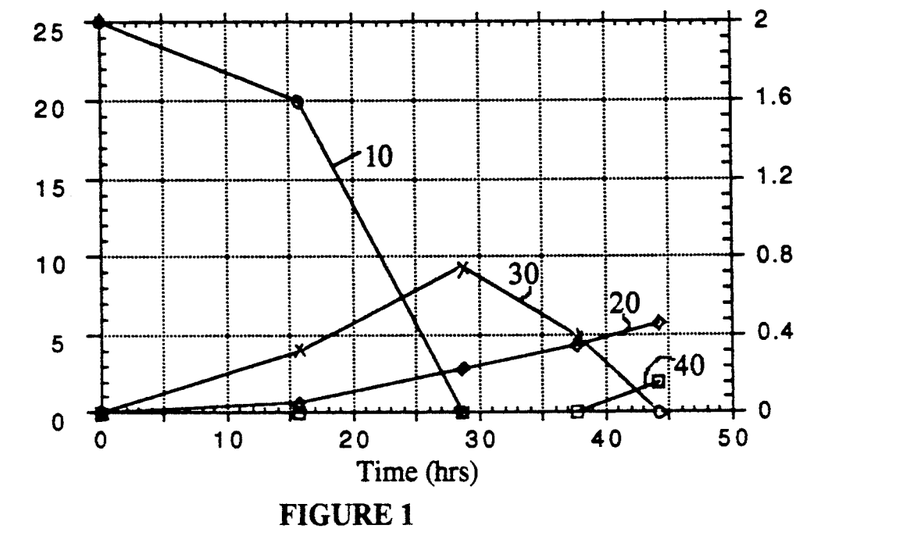
FIG. 1—Batch culture of YS2 strain at 25 g/l glucose, 5 g/l ammonium sulfate.

The results on batch culture behavior of the YS2 strain in a balanced synthetic nutrient medium containing 25 g/l of glucose are presented in FIG. 1 and Table 1.

The concentration of ammonium sulfate was 5 g/l. FIG. 1 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis).

Two phases of microbial growth are apparent in FIG. 1. In the first phase (0–28 h) glucose is consumed to produce cell mass and ethanol. In this phase no detectable amount of inositol was produced. In the second phase, ethanol was consumed to produce cell mass. About 170 mg/l of inositol was produced toward the end of the second phase.

TABLE 1

| Time | Glucose | Inositol | Cell Mass | Ethanol |
|---|---|---|---|---|
| 0.00 | 25 | 0 | 0.08 | 0 |
| 15.75 | 20 | 0 | 0.714 | 3.92 |
| 28.66 | 0 | 0 | 2.89 | 9.38 |
| 37.76 | 0 | 0 | 4.34 | 5.01 |
| 44.22 | 0 | 0.16 | 5.7 | 0 |

(Time in hours; all other values in grams/liter)

TABLE 2

| Time | Glucose | Inositol | Cell Mass | Ethanol |
|---|---|---|---|---|
| 0 | 50 | 0 | 0.05 | 0 |
| 22.9 | 3.34 | 0 | 3.138 | 23.37 |
| 47.9 | 0 | 0.15 | 9.1 | 0 |

(Time in hours; all other values in grams/liter)

Figure 2:
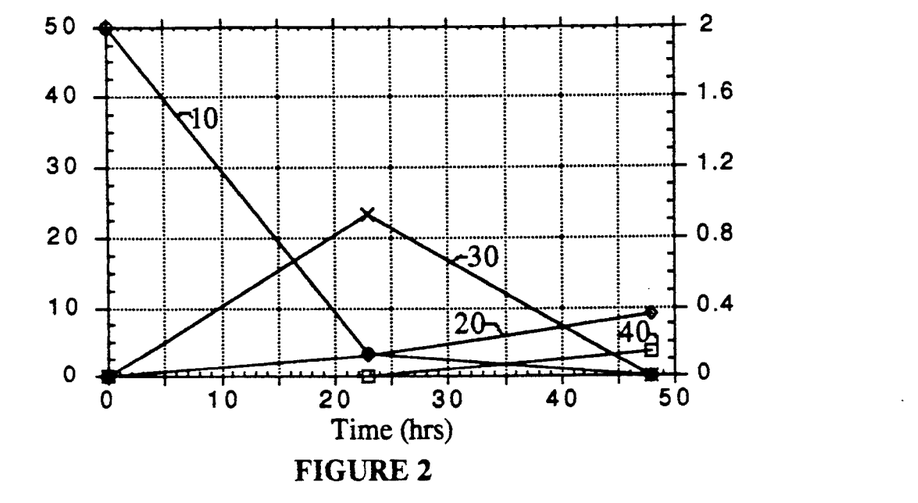
FIG. 2—Batch culture of YS2 strain at 50 g/l glucose, 10 g/l ammonium sulfate.

The results on batch culture behavior of the YS2 strain in a balanced synthetic nutrient medium containing 50 g/l of glucose are presented in FIG. 2 and Table 2. The ammonium sulfate concentration was 10 g/l. FIG. 2 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). Once again, two phases of microbial growth are apparent in FIG. 2. In the first phase (0—23 h) glucose is consumed to produce cell mass and ethanol. Once again, in the glucose consumption phase no detectable amount of inositol was produced. In the second phase, ethanol was consumed to produce cell mass. As in the previous experiment, about 170 mg/l of inositol was produced toward the end of the second phase.

Figure 3:
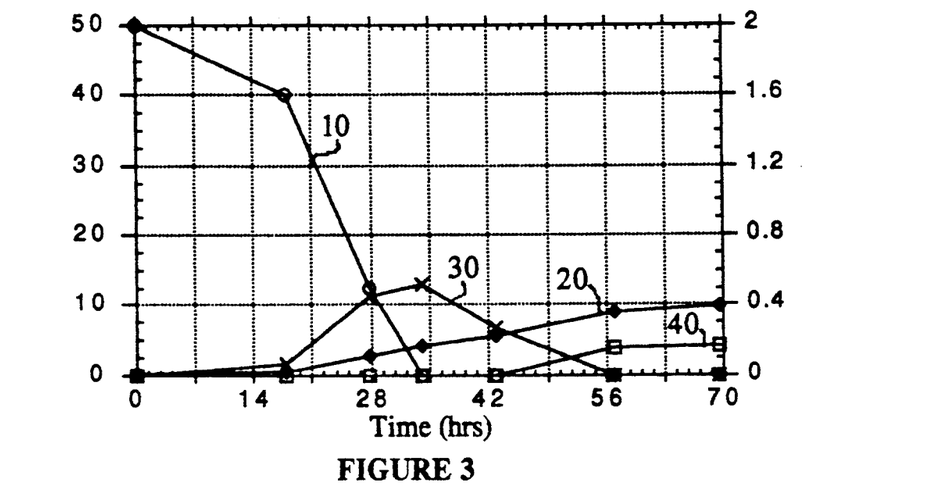
FIG. 3—Batch culture of YS2 strain at 50 g/l glucose, 5 g/l ammonium sulfate.

The results of the above two experiments illustrate that the amount of inositol produced at the end of a batch experiment is independent of the starting glucose concentration and that no inositol is produced in the glucose consumption phase. Furthermore, it was thought that in a balanced nutrient medium containing an excess of a nitrogen source (glucose/ammonium sulfate ratio of 5) glucose was consumed to preferentially produce cell mass and ethanol rather than inositol. Thus another batch experiment was conducted at initial glucose concentration of 50 g/l and with glucose to ammonium sulfate ratio of 10 instead of 5 as in the balanced nutrient medium. The results of this experiment are presented in FIG. 3 and Table 3. The ammonium sulfate concentration was 10 g/l. FIG. 3 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). Once again, two phases of microbial growth are apparent in FIG. 3. In the first phase (0–34 h) glucose is consumed to produce cell mass and ethanol. Once again, in the glucose consumption phase no detectable amount of inositol was produced. In the second phase, ethanol was consumed to produce cell mass. As in the previous two experiments, about 160-170 mg/l of inositol was produced toward the end of the second phase.

Comparison of results presented in FIGS. 2 and 3 illustrate that in the range of glucose/ammonium sulfate ratio of 5 to 10 there is no noticeable change in the batch fermentation behavior of the YS2 strain in the minimal media.

TABLE 3

| Time | Glucose | Inositol | Cell Mass | Ethanol |
|---|---|---|---|---|
| 0 | 50 | 0 | 0.1 | 0 |
| 18 | 40 | 0 | 0.536 | 1.64 |
| 27.75 | 12.4 | 0 | 2.852 | 11.33 |
| 34 | 0 | 0 | 4.086 | 12.91 |
| 42.91 | 0 | 0 | 5.6 | 6.84 |
| 56.9 | 0 | 0.16 | 9.108 | 0.03 |
| 69.5 | 0 | 0.17 | 9.786 | 0 |

(Time in hours; all other values in grams/liter)

TABLE 4

| Time | Glucose | Inositol | Cell Mass | Ethanol |
|---|---|---|---|---|
| 0 | 49.8 | 0 | 0.04 | 0 |
| 9.81 | 43.43 | 0 | 0.436 | 1.77 |
| 13.86 | 36.92 | 0 | 1 | 5.11 |
| 16.11 | 35.93 | 0 | 1.464 | 6.2 |
| 22.91 | 33.69 | 0 | 2.148 | 9.17 |
| 35.36 | 27.02 | 0 | 2.48 | 6.9 |
| 56.97 | 20.08 | 0 | 2.812 | 4.8 |
| 86.02 | 13.27 | 0 | 2.52 | 2.32 |
| 110.33 | 10.65 | 0 | 2.148 | 1.48 |
| 129.93 | 7.26 | 0 | 2.4 | 0.64 |
| 142.15 | 5.24 | 0 | 2.442 | 0.55 |
| 153.65 | 2.54 | 0 | 2.418 | 0.5 |
| 167.65 | 0 | 0.1 | 2.662 | 0.37 |
| 177.65 | 0 | 0.15 | 2.644 | 0.25 |
| 191.65 | 0 | 0.16 | 2.812 | 0 |

(Time in hours; all other values in grams/liter)

Figure 4:
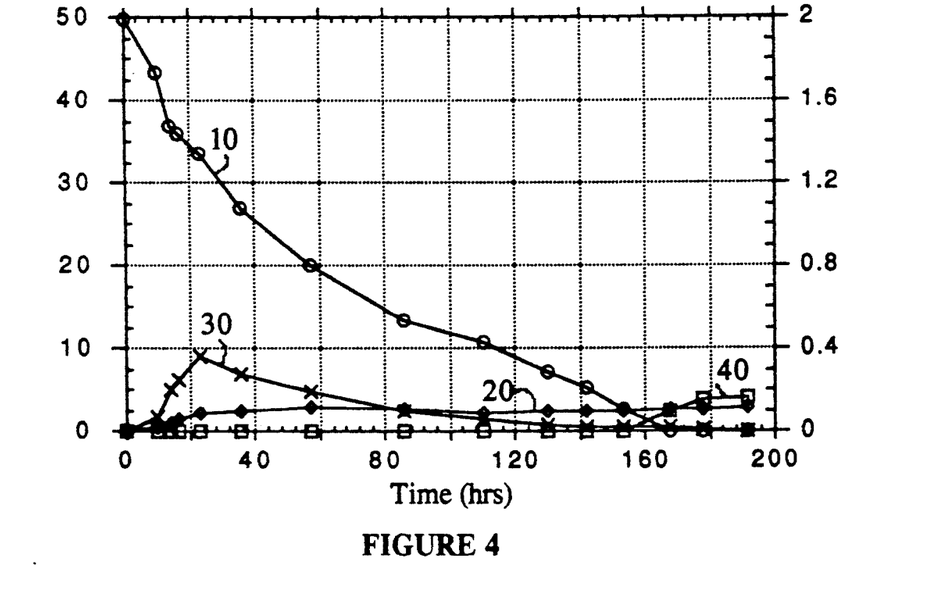
FIG. 4—Batch culture of YS2 strain at 50 g/l glucose, 0.5 g/l ammonium sulfate.

FIG. 4 and Table 4 illustrate the results of batch culture behavior of the YS2 strain in a severely nitrogen-limited synthetic nutrient medium (glucose/ammonium sulfate of 500). The ammonium sulfate concentration was 0.1 g/l. FIG. 4 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). FIG. 4 indicates the presence of two fermentation phases. In the first phase (0-24 h) a portion of glucose was consumed to produce cell mass and ethanol. No detectable amount of inositol was produced in this plase. In the second phase, the microorganisms slowly but simultaneously oxidized glucose and ethanol to $CO_2$. There was little or no growth of cells in this phase. Inositol in the amount of 150-170 mg/l was produced toward the end of the second phase. A severe nitrogen limitation prevented the formation of additional cell mass and ethanol in the second fermentation phase. Thus in the second phase there was an excess of glucose and ethanol which could not be converted to additional cell mass due to nitrogen limitation. In spite of this, the excess glucose in the second phase did not lead to increased inositol production. Instead, the microbial cells oxidized the excess glucose to $CO_2$. Only toward the end of the second phase, when the glucose concentration fell to non-detectable levels, was there any production of free inositol in the culture. These results led to the conclusion that only under a glucose-limited condition can the YS2 strain be made to produce free inositol.

Figure 5:
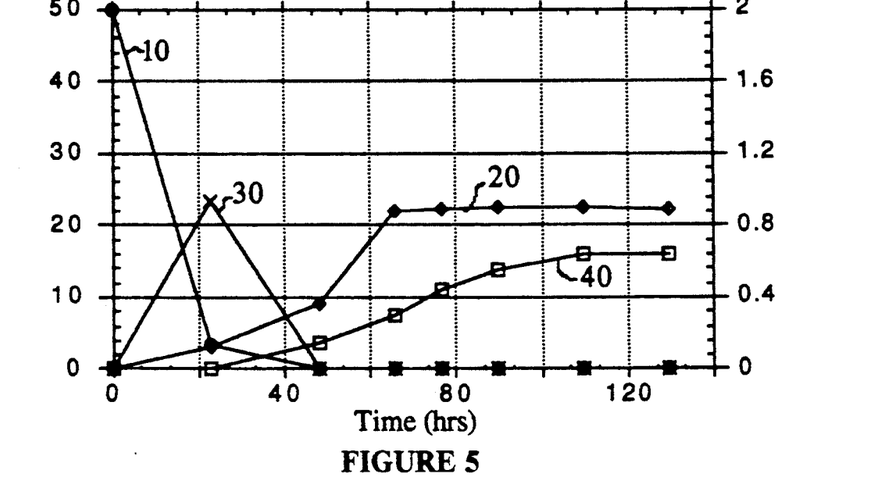
FIG. 5—Continuous culture of YS2 strain at 50 g/l glucose, 10 g/l ammonium sulfate; D=0.1 per hour beginning at about 50 hours.

A glucose-limited condition can be achieved by operating a fermenter in a semi-batch or continuous mode. To take advantage of this observation, the YS2 strain was cultivated under a glucose-limited condition in a continuous culture at $D=0.1$ /h, feed glucose concentration of 50 g/l and glucose to ammonium sulfate ratio of 5. Dilution rate "D" is a concept well known to those skilled in the art. See, e.g., J. Bailey and D. Ollis, *Biochemical Engineering Fundamentals*, pp. 579-580, McGraw-Hill (1986). The results of this experiment are shown in FIG. 5 and Table 5. The ammonium sulfate concentration was 10 g/l. Dilution rate D was 0.1 per hour beginning at about 50 hours. FIG. 5 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). At the end of the batch phase (about 50 h), the culture contained about 170 mg/l of inositol. Soon after the batch phase, the continuous mode was initiated. In the continuous mode, the concentration of glucose in the culture medium was always below detectable limits. In the continuous mode, the inositol concentration in the culture increased from 170 mg/l to about 640 mg/l.

TABLE 5

| Time | Glucose | Inositol | Cell Mass | Ethanol |
| --- | --- | --- | --- | --- |
| 0 | 50 | 0 | 0.05 | 0 |
| 22.9 | 3.34 | 0 | 3.138 | 23.37 |
| 47.9 | 0 | 0.15 | 9.1 | 0 |
| 65.54 | 0.005 | 0.3 | 22.004 | 0.22 |
| 76.55 | 0.005 | 0.44 | 22.38 | 0.005 |
| 89.71 | 0.005 | 0.55 | 22.58 | 0.005 |
| 109.71 | 0.005 | 0.64 | 22.5 | 0.005 |
| 129.60 | 0.005 | 0.64 | 22.4 | 0.005 |

(Time in hours; all other values in grams/liter)

TABLE 6

| Time | Glucose | Inositol | Cell Mass | Ethanol |
| --- | --- | --- | --- | --- |
| 0 | 25 | 0 | 0.08 | 0 |
| 15.75 | 20 | 0 | 0.714 | 3.92 |
| 28.66 | 0 | 0 | 2.89 | 9.38 |
| 37.76 | 0 | 0.05 | 4.34 | 5.01 |
| 44.22 | 0 | 0.16 | 5.7 | 0 |
| 52.17 | 0.005 | 0.23 | 14.734 | 0.005 |
| 59.97 | 0.005 | 0.59 | 26.76 | 0.005 |
| 66.97 | 0.005 | 1.16 | 30.618 | 0.005 |
| 72.87 | 0.005 | 1.56 | 30.136 | 0.005 |
| 84.78 | 0.005 | 1.47 | 29.046 | 0.005 |
| 91.28 | 0.005 | 1.57 | 30.688 | 0.005 |
| 100.13 | 0.005 | 1.66 | 30.688 | 0.005 |
| 109.84 | 0.005 | 1.68 | 31.804 | 0.005 |

(Time in hours; all other values in grams/liter)

Figure 6:
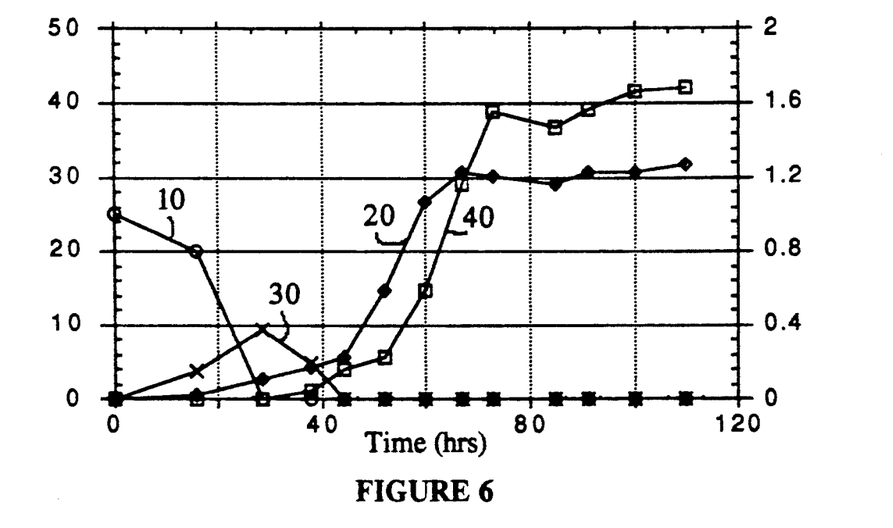
FIG. 6—Continuous culture of YS2 strain at 100 g/l glucose, 10 g/l ammonium sulfate; D=0.05 per hour beginning at about 45 hours.

Another glucose-limited continuous culture experiment was conducted at higher feed glucose concentration of 100 g/l with $D=0.05$ but initial glucose/ammonium sulfate ratio of 5 as in the previous experiment. The results of this experiment are described in FIG. 6 and Table 6. The ammonium sulfate concentration was 5 g/l. Dilution rate D was 0.05 per hour beginning at about 45 hours. FIG. 6 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). The results show that with an increase in feed glucose concentration to 100 g/l the inositol production in the culture could be increased to 1680 mg/l.

Further increase in feed glucose concentration led to formation of an excess glucose condition in the continuous culture. As a result, the production of inositol decreased as glucose concentration in the feed was further increased.

Figure 7A:
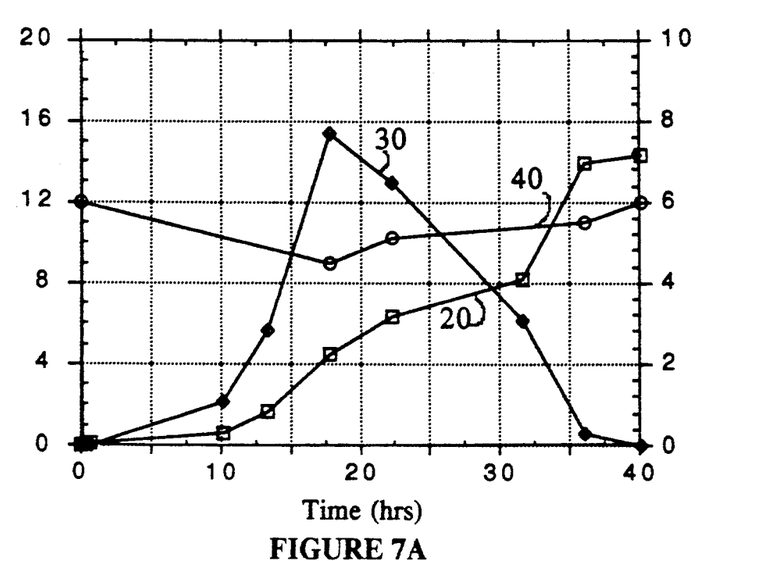
FIG. 7A, 7B—Batch culture of YS2 strain in 12° Brix almond hull juice (AHJ).
Figure 7B:
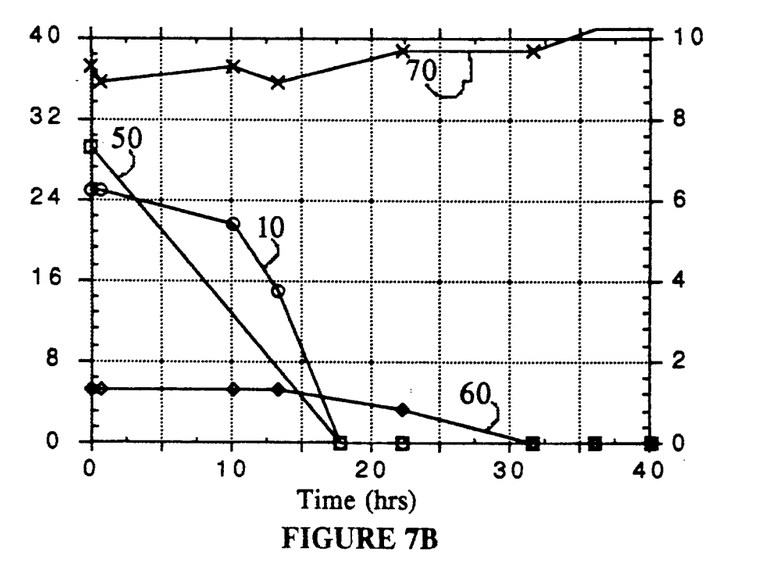

The batch culture behavior of the YS2 strain in a 12° Brix almond hull juice (AHJ) is presented in FIGS. 7A and 7B and Table 7. FIG. 7A illustrates cell mass level 20 (g/l, left vertical axis), ethanol concentration 30 (g/l, left vertical axis), and inositol concentration 40 (g/l, right vertical axis) over time (hours, horizontal axis). FIG. 7B illustrates glucose concentration 10 (g/l, left vertical axis), fructose concentration 50 (g/l, left vertical axis), sucrose concentration 60 (g/l, left vertical axis), and sorbitol concentration 70 (g/l, right vertical axis) over time (hours, horizontal axis). Two phases of growth were observed. In the first phase (0-18 h), glucose, fructose and sucrose were consumed to produce cell mass and ethanol. The inositol concentration slightly decreased during this phase. In the second phase, the cells consumed ethanol to produce additional cell mass. The inositol concentration slightly increased during this phase. Overall, there was no measurable increase in the inositol concentration in the medium. There was a noticeable increase in the sorbitol concentration. The inositol and sorbitol can be isolated from the medium and separately purified.

TABLE 7

| Time | Glucose | Fructose | Sucrose | Sorbitol | Inositol | Cell Mass | Ethanol |
| --- | --- | --- | --- | --- | --- | --- | --- |
| 0 | 25 | 29.3 | 5.2 | 9.3 | 6 | 0 | 0 |
| 0.6 | 25 |  | 5.2 | 8.9 |  | 0.084 | 0 |
| 10.16 | 21.6 |  | 5.3 | 9.3 |  | 0.61 | 2.17 |
| 13.42 | 15 |  | 5.3 | 8.9 |  | 1.624 | 5.66 |
| 17.82 | 0 | 0 |  |  | 4.5 | 4.512 | 15.35 |
| 22.27 | 0 | 0 | 3.3 | 9.7 | 5.1 | 6.334 | 12.99 |
| 31.63 | 0 | 0 | 0 | 9.7 |  | 8.216 | 6.12 |
| 36.14 | 0 |  | 0 | 10.2 | 5.5 | 13.91 | 0.62 |

TABLE 7-continued

| Time | Glucose | Fructose | Sucrose | Sorbitol | Inositol | Cell Mass | Ethanol |
|---|---|---|---|---|---|---|---|
| 40.2 | 0 | 0 | 0 | 10.2 | 6 | 14.354 | 0 |

(Time in hours; all other values in grams/liter)

TABLE 8

| Time | Glucose | Fructose | Sucrose | Sorbitol | Inositol | Cell Mass | Ethanol |
|---|---|---|---|---|---|---|---|
| 38.89 | 0.005 | 0.005 | 0.005 | 10.6 | 5.3 | 10.38 | 0.18 |
| 43.09 | 0.005 | 0.005 | 0.005 | 10.5 | 5.8 | 6.264 | 5.16 |
| 45.15 | 0.005 | 0.005 | 0.005 | 10.4 | 5.6 | 5.83 | 7.94 |
| 49.6 | 0.005 | 0.005 | 0.005 | 10.1 | 5.7 | 5.592 | 12.56 |
| 55.86 | 0.005 | 0.005 | 0.005 | 10.1 | 5.8 | 5.592 | 14.19 |
| 63.3 | 0.005 | 0.005 | 0.005 | 10.8 | 6.3 | 5.396 | 15.13 |
| 66.9 | 0.005 | 0.005 | 0.005 | 10.7 | 6.4 | 5.592 | 15.88 |
| 73.3 | 0.005 | 0.005 | 0.005 | 10.7 | 6.2 | 5.474 | 16.4 |
| 79.43 | 0.005 | 0.005 | 0.005 | 10.2 | 7.2 | 6.234 |  |
| 87.91 | 0.005 | 0.005 | 0.005 | 10 | 7.8 | 7.36 | 14.9 |
| 92.86 | 0.005 | 0.005 | 0.005 | 9.5 | 8 | 10.556 | 13.9 |
| 95.97 | 0.005 | 0.005 | 0.005 | 10.2 | 8.2 | 10.694 |  |
| 99.58 | 0.005 | 0.005 | 0.005 | 9.2 | 8.3 | 12.622 | 11.13 |
| 110.6 | 0.005 | 0.005 | 0.005 | 9.5 | 8.9 | 13.28 |  |
| 115.45 | 0.005 | 0.005 | 0.005 | 9.6 | 8.5 | 13.992 | 8.6 |
| 119.81 | 0.005 | 0.005 | 0.005 |  |  | 14.58 | 7.9 |
| 134.4 | 0.005 | 0.005 | 0.005 | 10 | 9 | 13.78 | 7.2 |

(Time in hours; all other values in grams/liter)

Figure 8:
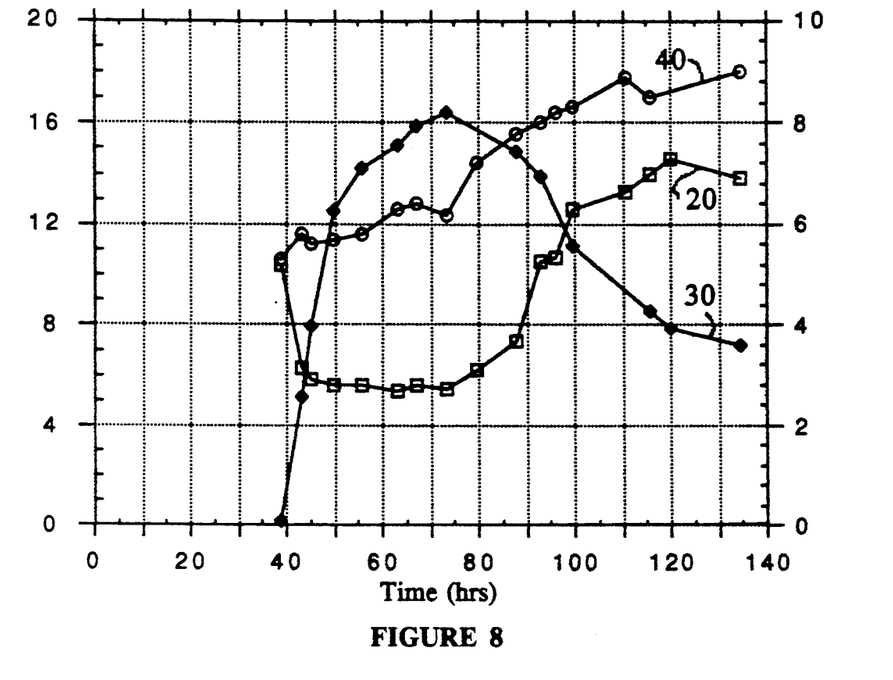
FIG. 8—Continuous culture of YS2 strain in 12° Brix AHJ, 0 to 15 g/l ammonium sulfate at 71 hours; D=0.1 per hour beginning at about 40 hours.

FIG. 8 and Table 8 present the continuous fermentation behavior of the YS2 strain in 12° Brix AHJ. Dilution rate D was 0.1 per hour beginning at about 40 hours. FIG. 8 illustrates cell mass level 20 (g/l, left vertical axis), ethanol concentration 30 (g/l, left vertical axis), and inositol concentration 40 (g/l, right vertical axis) over time (hours, horizontal axis). The continuous fermentation was conducted at D=0.1 (l/h) with and without the addition of the nitrogen source, ammonium sulfate. At the end of the batch phase (after about 40 h) continuous mode was initiated by using unmodified AHJ. At about 71 h, the continuous reactor was fed AHJ supplemented with 15 g/l of ammonium sulfate. The concentration of inositol increased only slightly during fermentation in unmodified AHJ. However, it increased from 6.2 to 9.0 g/l during fermentation in modified AHJ indicating the production of inositol by YS2 in the modified AHJ.

Figure 9:
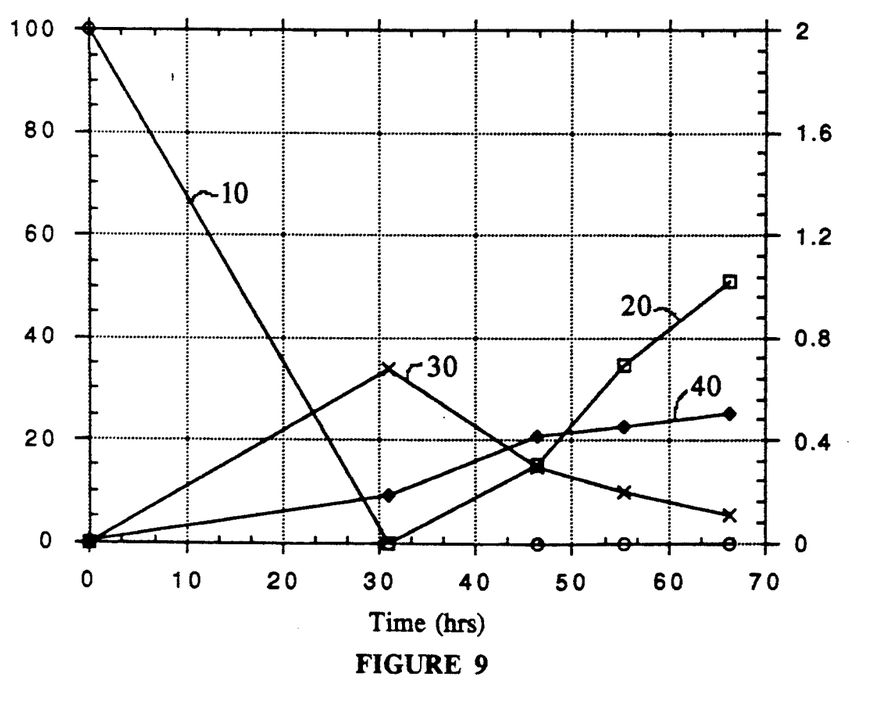
FIG. 9—Batch culture of YS3 strain at 100 g/l glucose, 10 g/l ammonium sulfate.

FIG. 9 and Table 9 present the results on batch culture behavior of the YS3 strain in a balanced synthetic nutrient medium containing 100 g/l of glucose and 10 g/l of ammonium sulfate. FIG. 9 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). Two phases of microbial growth are apparent in FIG. 9. In the first phase (0–31 h) glucose was consumed to produce cell mass and ethanol. In this phase no detectable amount of inositol was produced. In the second phase, ethanol was consumed to produce cell mass. About 1.02 g/l of inositol was produced toward the end of the second phase. Since no inositol was produced as long as a detectable amount of glucose was present in the culture, it was concluded that, like the YS2 strain, the YS3 strain produced inositol only under glucose-limited conditions. Compare these results to those in Tables 1 and 2, using the YS2 strain in balanced synthetic media containing 25 and 50 g/l glucose, respectively.

TABLE 9

| Time | Glucose | Inositol | Cell Mass | Ethanol |
|---|---|---|---|---|
| 0 | 100 | 0 | 0.088 | 0 |
| 30.9 | 0 | 0 | 9.08 | 33.7 |
| 46.35 | 0 | 0.3 | 20.64 | 14.7 |
| 55.3 | 0 | 0.69 | 22.76 | 9.8 |
| 66.35 | 0 | 1.02 | 25.23 | 5.5 |

(Time in hours; all other values in grams/liter)

Figure 10:
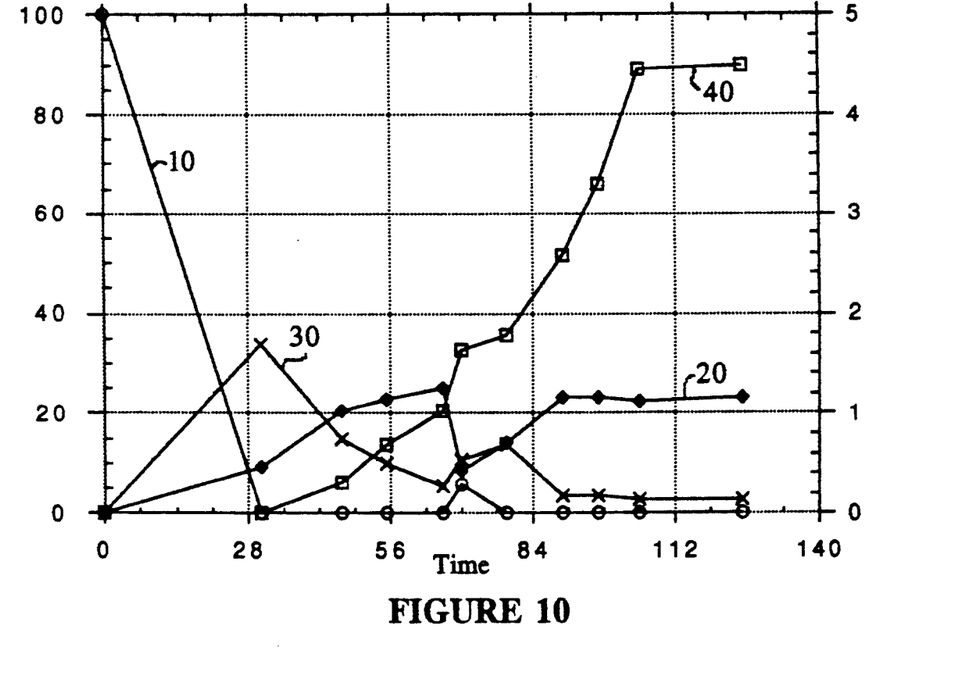
FIG. 10—Continuous culture of YS3 strain at 100 g/l glucose, 10 g/l ammonium sulfate; D=0.025 per hour beginning at about 70 hours.

To take advantage of this, the YS3 strain was cultivated under glucose-limited conditions in a continuous culture at D=0.025 per hour, feed glucose concentration of 100 g/l and glucose to ammonium sulfate ratio of 10. The results of this experiment are shown in FIG. 10 and Table 10. The ammonium sulfate concentration was 10 g/l. Dilution rate D was 0.025 per hour beginning at about 70 hours. FIG. 10 illustrates glucose concentration 10 (g/l, left vertical axis), cell mass level 20 (g/l, left vertical axis), ethanol concentration 30 (g/l, left vertical axis), and inositol concentration 40 (g/l, right vertical axis) over time (hours, horizontal axis). At the end of the batch phase (about 67 h), the culture contained about 1.02 g/l of inositol. At about 70 h, the continuous mode was initiated. In switching to continuous mode, the cells were stirred and partially removed, but soon returned to stable levels. In the continuous mode, the glucose in the culture medium settled below the detectable limits. In the continuous mode, the inositol concentration in the culture increased from 1.02 g/l to about 4.45 g/l. Compare these results to those in Table 6, using the YS2 strain in a glucose-limited continuous culture with a feed glucose concentration of 100 g/l with D=0.05 per hour.

TABLE 10

| Time | Glucose | Inositol | Cell Mass | Ethanol |
|---|---|---|---|---|
| 0 | 100 | 0 | 0.088 | 0 |
| 30.9 | 0 | 0 | 9.08 | 33.7 |
| 46.35 | 0 | 0.3 | 20.64 | 14.7 |
| 55.3 | 0 | 0.69 | 22.76 | 9.8 |
| 66.35 | 0 | 1.02 | 25.23 | 5.5 |
| 70.1 | 5.76 | 1.63 | 8.56 | 10.8 |
| 78.85 | 0 | 1.78 | 14.08 | 13.8 |
| 89.75 | 0 | 2.58 | 23.28 | 3.4 |
| 97 | 0 | 3.3 | 23.28 | 3.5 |

TABLE 10-continued

| Time | Glucose | Inositol | Cell Mass | Ethanol |
|---|---|---|---|---|
| 105 | 0 | 4.46 | 22.56 | 2.8 |
| 125 | 0 | 4.5 | 23 | 2.75 |

(Time in hours; all other values in grams/liter)

One skilled in the art will recognize that these teachings can be applied in other ways, including the use of other plant juices as a medium. These juices include corn steep liquor, cane sugar molasses, beet sugar molasses, sorghum molasses, wood molasses, cherry juice, plum juice, prune juice, pineapple juice, citrus juice or apple juice. Although the invention has been described in detail in the foregoing embodiments for the purpose of illustration, one skilled in the art will recognize how to practice variations on these teachings that come within the scope of the following claims.

What is claimed is:

1. A method of increasing production of inositol in a culture medium comprising:
   providing a culture medium suitable for growth of microorganisms, comprising a source of carbon and a source of nitrogen,
   inoculating said medium with Saccharomyces cerevisiae YS2 or Saccharomyces cerevisiae YS3,
   culturing said strain in the medium to produce ethanol,
   continuing said culturing until the concentration of glucose reaches less than about 5 grams per liter, then further continuing said culturing to permit consumption of ethanol, and
   isolating inositol from the reaction medium.

2. The method of claim 1 wherein said medium is a balanced synthetic medium.

3. The method of claim 1 wherein said medium is selected from the group consisting of corn steep liquor, cane sugar molasses, beet sugar molasses, sorghum molasses, wood molasses, cherry juice, plum juice, prune juice, pineapple juice, citrus juice and apple juice.

4. The method of claim 1 wherein said medium is almond hull juice.

5. The method of claim 1 wherein said source of carbon is glucose.

6. The method of claim 1 wherein said source of nitrogen is ammonium sulfate.

7. The method of claim 1 where said culturing is performed in continuous culture.

8. The method of claim 10 wherein said continuous culture is conducted at dilution D in the range of approximately 0.001 to about 0.22 per hour.

9. The method of claim 1 where said culturing is performed in batch.

10. The method of claim 1 where said culturing is a combination of continuous and batch culture.

11. The method of claim 1 further comprising continuing said culturing until the concentration of ethanol decreases below about 5 g/L.

* * * * *